(12) United States Patent
Salter et al.

(10) Patent No.: US 10,502,690 B2
(45) Date of Patent: Dec. 10, 2019

(54) INDICATOR SYSTEM FOR VEHICLE WEAR COMPONENTS

(71) Applicant: Ford Global Technologies, LLC, Dearborn, MI (US)

(72) Inventors: Stuart C. Salter, White Lake, MI (US); Terry R. Lobsinger, Farmington Hills, MI (US); James J. Surman, Clinton Township, MI (US); Paul Kenneth Dellock, Northville, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 93 days.

(21) Appl. No.: 15/652,707

(22) Filed: Jul. 18, 2017

(65) Prior Publication Data

US 2019/0025225 A1 Jan. 24, 2019

(51) Int. Cl.
| | | |
|---|---|---|
| *G01N 21/88* | (2006.01) | |
| *B60Q 3/30* | (2017.01) | |
| *G01M 13/023* | (2019.01) | |
| *B60Q 3/70* | (2017.01) | |
| *F02B 77/08* | (2006.01) | |
| *G01N 21/64* | (2006.01) | |
| *G01N 21/892* | (2006.01) | |
| *G01M 15/04* | (2006.01) | |

(52) U.S. Cl.
CPC ......... *G01N 21/8806* (2013.01); *B60Q 3/30* (2017.02); *B60Q 3/70* (2017.02); *F02B 77/081* (2013.01); *G01M 13/023* (2013.01); *G01M 15/042* (2013.01); *G01N 21/64* (2013.01); *G01N 21/892* (2013.01); *G01N 2201/062* (2013.01)

(58) Field of Classification Search
CPC ...... G01N 21/8806; G01N 21/64; B60Q 3/30; B60Q 3/70; F02B 77/081
See application file for complete search history.

(56) References Cited

U.S. PATENT DOCUMENTS

| | | | |
|---|---|---|---|
| 2,486,859 A | 11/1949 | Meijer et al. | |
| 5,053,930 A | 10/1991 | Benavides | |
| 5,434,013 A | 7/1995 | Fernandez | |
| 5,709,453 A | 1/1998 | Krent et al. | |
| 5,839,718 A | 11/1998 | Hase et al. | |
| 5,994,712 A * | 11/1999 | Mack .................. | G01N 21/894 250/559.42 |

(Continued)

FOREIGN PATENT DOCUMENTS

| | | |
|---|---|---|
| CN | 101337492 A | 1/2009 |
| CN | 201169230 Y | 2/2009 |

(Continued)

*Primary Examiner* — David P Porta
*Assistant Examiner* — Jeremy S Valentiner
(74) *Attorney, Agent, or Firm* — Geoffrey Brumbaugh; Price Heneveld LLP (57) ABSTRACT

An illumination apparatus for a vehicle is disclosed. The illumination apparatus comprises a wear component comprising a plurality of layers disposed in an engine compartment. The layers comprise a photoluminescent portion and a cover layer disposed over the photoluminescent portion. The apparatus further comprises a light source located in the engine compartment. The light source is configured to emit an excitation emission configured to illuminate the photoluminescent portion to emit an output emission having a color different than the excitation emission.

17 Claims, 5 Drawing Sheets

(56) References Cited

U.S. PATENT DOCUMENTS

| | | | |
|---|---|---|---|
| 6,031,511 A | 2/2000 | DeLuca et al. | |
| 6,117,362 A | 9/2000 | Yen et al. | |
| 6,294,990 B1 | 9/2001 | Knoll et al. | |
| 6,419,854 B1 | 7/2002 | Yocom et al. | |
| 6,494,490 B1 | 12/2002 | Trantoul | |
| 6,532,810 B1* | 3/2003 | Ahmed | G01M 13/023 73/114.77 |
| 6,577,073 B2 | 6/2003 | Shimizu et al. | |
| 6,729,738 B2 | 5/2004 | Fuwausa et al. | |
| 6,737,964 B2 | 5/2004 | Samman et al. | |
| 6,773,129 B2 | 8/2004 | Anderson, Jr. et al. | |
| 6,820,888 B1 | 11/2004 | Griffin | |
| 6,851,840 B2 | 2/2005 | Ramamurthy et al. | |
| 6,859,148 B2 | 2/2005 | Miller | |
| 6,871,986 B2 | 3/2005 | Yamanaka et al. | |
| 6,943,672 B2 | 9/2005 | Choi | |
| 6,953,536 B2 | 10/2005 | Yen et al. | |
| 6,990,922 B2 | 1/2006 | Ichikawa et al. | |
| 7,015,893 B2 | 3/2006 | Li et al. | |
| 7,161,472 B2 | 1/2007 | Strumolo et al. | |
| 7,213,923 B2 | 5/2007 | Liu et al. | |
| 7,216,997 B2 | 5/2007 | Anderson, Jr. | |
| 7,249,869 B2 | 7/2007 | Takahashi et al. | |
| 7,264,366 B2 | 9/2007 | Hulse | |
| 7,264,367 B2 | 9/2007 | Hulse | |
| 7,347,576 B2 | 3/2008 | Wang et al. | |
| 7,441,914 B2 | 10/2008 | Palmer et al. | |
| 7,501,749 B2 | 3/2009 | Takeda et al. | |
| 7,575,349 B2 | 8/2009 | Bucher et al. | |
| 7,635,212 B2 | 12/2009 | Seidler | |
| 7,726,856 B2 | 6/2010 | Tsutsumi | |
| 7,745,818 B2 | 6/2010 | Sofue et al. | |
| 7,753,541 B2 | 7/2010 | Chen et al. | |
| 7,834,548 B2 | 11/2010 | Jousse et al. | |
| 7,862,220 B2 | 1/2011 | Cannon et al. | |
| 7,987,030 B2 | 7/2011 | Flores et al. | |
| 8,016,465 B2 | 9/2011 | Egerer et al. | |
| 8,022,818 B2 | 9/2011 | la Tendresse et al. | |
| 8,044,415 B2 | 10/2011 | Messere et al. | |
| 8,066,416 B2 | 11/2011 | Bucher | |
| 8,071,988 B2 | 12/2011 | Lee et al. | |
| 8,097,843 B2 | 1/2012 | Agrawal et al. | |
| 8,118,441 B2 | 2/2012 | Hessling | |
| 8,120,236 B2 | 2/2012 | Auday et al. | |
| 8,136,425 B2 | 3/2012 | Bostick | |
| 8,163,201 B2 | 4/2012 | Agrawal et al. | |
| 8,169,131 B2 | 5/2012 | Murazaki et al. | |
| 8,178,852 B2 | 5/2012 | Kingsley et al. | |
| 8,197,105 B2 | 6/2012 | Yang | |
| 8,203,260 B2 | 6/2012 | Li et al. | |
| 8,207,511 B2 | 6/2012 | Bortz et al. | |
| 8,232,533 B2 | 7/2012 | Kingsley et al. | |
| 8,247,761 B1 | 8/2012 | Agrawal et al. | |
| 8,261,686 B2 | 9/2012 | Birman et al. | |
| 8,286,378 B2 | 10/2012 | Martin et al. | |
| 8,317,329 B2 | 11/2012 | Seder et al. | |
| 8,317,359 B2 | 11/2012 | Harbers et al. | |
| 8,408,766 B2 | 4/2013 | Wilson et al. | |
| 8,415,642 B2 | 4/2013 | Kingsley et al. | |
| 8,421,811 B2 | 4/2013 | Odland et al. | |
| 8,459,832 B2 | 6/2013 | Kim | |
| 8,466,438 B2 | 6/2013 | Lambert et al. | |
| 8,519,359 B2 | 8/2013 | Kingsley et al. | |
| 8,519,362 B2 | 8/2013 | Labrot et al. | |
| 8,539,702 B2 | 9/2013 | Li et al. | |
| 8,552,848 B2 | 10/2013 | Rao et al. | |
| 8,606,430 B2 | 12/2013 | Seder et al. | |
| 8,624,716 B2 | 1/2014 | Englander | |
| 8,631,598 B2 | 1/2014 | Li et al. | |
| 8,653,553 B2 | 2/2014 | Yamazaki et al. | |
| 8,664,624 B2 | 3/2014 | Kingsley et al. | |
| 8,683,722 B1 | 4/2014 | Cowan | |
| 8,724,054 B2 | 5/2014 | Jones | |
| 8,754,426 B2 | 6/2014 | Marx et al. | |
| 8,755,589 B2 | 6/2014 | Sobczak et al. | |
| 8,773,012 B2 | 7/2014 | Ryu et al. | |
| 8,846,184 B2 | 9/2014 | Agrawal et al. | |
| 8,851,694 B2 | 10/2014 | Harada | |
| 8,876,352 B2 | 11/2014 | Robbins et al. | |
| 8,905,610 B2 | 12/2014 | Coleman et al. | |
| 8,952,341 B2 | 2/2015 | Kingsley et al. | |
| 8,994,495 B2 | 3/2015 | Dassanayake et al. | |
| 9,006,751 B2 | 4/2015 | Kleo et al. | |
| 9,018,833 B2 | 4/2015 | Lowenthan et al. | |
| 9,057,021 B2 | 6/2015 | Kingsley et al. | |
| 9,059,378 B2 | 6/2015 | Verger et al. | |
| 9,065,447 B2 | 6/2015 | Buttolo et al. | |
| 9,067,530 B2 | 6/2015 | Bayersdorfer et al. | |
| 9,187,034 B2 | 11/2015 | Tarahomi et al. | |
| 9,240,115 B2 | 1/2016 | Omura et al. | |
| 9,299,887 B2 | 3/2016 | Lowenthal et al. | |
| 9,315,148 B2 | 4/2016 | Schwenke et al. | |
| 9,376,058 B2 | 6/2016 | Salter | |
| 9,393,903 B2 | 7/2016 | Salter et al. | |
| 9,393,904 B2 | 7/2016 | Salter et al. | |
| 9,393,905 B2 | 7/2016 | Salter et al. | |
| 9,434,304 B2 | 9/2016 | Salter et al. | |
| 9,452,709 B2 | 9/2016 | Aburto Crespo | |
| 9,568,659 B2 | 2/2017 | Verger et al. | |
| 9,573,519 B1* | 2/2017 | Salter | F04D 27/001 |
| 9,616,812 B2 | 4/2017 | Sawayanagi | |
| 2002/0159741 A1 | 10/2002 | Graves et al. | |
| 2002/0163792 A1 | 11/2002 | Formoso | |
| 2003/0167668 A1 | 9/2003 | Kuks et al. | |
| 2003/0179548 A1 | 9/2003 | Becker et al. | |
| 2004/0213088 A1 | 10/2004 | Fuwausa | |
| 2005/0084229 A1 | 4/2005 | Babbitt et al. | |
| 2005/0189795 A1 | 9/2005 | Roessler | |
| 2006/0087826 A1 | 4/2006 | Anderson, Jr. | |
| 2006/0097121 A1 | 5/2006 | Fugate | |
| 2007/0032319 A1 | 2/2007 | Tufte | |
| 2007/0285938 A1 | 12/2007 | Palmer et al. | |
| 2007/0297045 A1 | 12/2007 | Sakai et al. | |
| 2008/0205075 A1 | 8/2008 | Hikmet et al. | |
| 2009/0217970 A1 | 9/2009 | Zimmerman et al. | |
| 2009/0219730 A1 | 9/2009 | Syfert et al. | |
| 2009/0251920 A1 | 10/2009 | Kino et al. | |
| 2009/0260562 A1 | 10/2009 | Folstad et al. | |
| 2009/0262515 A1 | 10/2009 | Lee et al. | |
| 2010/0102736 A1 | 4/2010 | Hessling | |
| 2011/0012062 A1 | 1/2011 | Agrawal et al. | |
| 2011/0133923 A1* | 6/2011 | Evans | B60T 17/221 340/454 |
| 2011/0265360 A1 | 11/2011 | Podd et al. | |
| 2011/0305919 A1* | 12/2011 | Conroy | C25D 5/10 428/615 |
| 2012/0001406 A1 | 1/2012 | Paxton et al. | |
| 2012/0104954 A1 | 5/2012 | Huang | |
| 2012/0183677 A1 | 7/2012 | Agrawal et al. | |
| 2012/0280528 A1 | 11/2012 | Dellock et al. | |
| 2013/0050979 A1 | 2/2013 | Van De Ven et al. | |
| 2013/0092965 A1 | 4/2013 | Kijima et al. | |
| 2013/0335994 A1 | 12/2013 | Mulder et al. | |
| 2013/0345946 A1* | 12/2013 | Omura | G01M 13/023 701/102 |
| 2014/0003044 A1 | 1/2014 | Harbers et al. | |
| 2014/0029281 A1 | 1/2014 | Suckling et al. | |
| 2014/0065442 A1 | 3/2014 | Kingsley et al. | |
| 2014/0103258 A1 | 4/2014 | Agrawal et al. | |
| 2014/0211498 A1 | 7/2014 | Cannon et al. | |
| 2014/0264396 A1 | 9/2014 | Lowenthal et al. | |
| 2014/0266666 A1 | 9/2014 | Habibi | |
| 2014/0373898 A1 | 12/2014 | Rogers et al. | |
| 2015/0046027 A1 | 2/2015 | Sura et al. | |
| 2015/0085488 A1 | 3/2015 | Grote, III et al. | |
| 2015/0109602 A1 | 4/2015 | Martin et al. | |
| 2015/0138789 A1 | 5/2015 | Singer et al. | |
| 2015/0267881 A1 | 9/2015 | Salter et al. | |
| 2015/0307033 A1 | 10/2015 | Preisler et al. | |
| 2016/0016506 A1 | 1/2016 | Collins et al. | |
| 2016/0102819 A1 | 4/2016 | Misawa et al. | |
| 2016/0131327 A1 | 5/2016 | Moon et al. | |
| 2016/0236613 A1 | 8/2016 | Trier | |
| 2016/0240794 A1 | 8/2016 | Yamada et al. | |

(56) References Cited

U.S. PATENT DOCUMENTS

| | | | |
|---|---|---|---|
| 2017/0158125 A1 | 6/2017 | Schuett et al. | |
| 2017/0253179 A1 | 9/2017 | Kumada | |
| 2018/0002039 A1* | 1/2018 | Finn | B64F 5/60 |

FOREIGN PATENT DOCUMENTS

| | | |
|---|---|---|
| CN | 201193011 Y | 2/2009 |
| CN | 204127823 U | 1/2015 |
| DE | 4120677 A1 | 1/1992 |
| DE | 29708699 U1 | 7/1997 |
| DE | 10319396 A1 | 11/2004 |
| EP | 1793261 A1 | 6/2007 |
| EP | 2778209 A1 | 9/2014 |
| JP | 2000159011 A | 6/2000 |
| JP | 2006170998 A | 6/2006 |
| JP | 2007238063 A | 9/2007 |
| KR | 20060026531 A | 3/2006 |
| WO | 2006047306 A1 | 5/2006 |
| WO | 2014068440 A1 | 5/2014 |
| WO | 2014161927 A1 | 10/2014 |

* cited by examiner

INDICATOR SYSTEM FOR VEHICLE WEAR COMPONENTS

FIELD OF THE INVENTION

The present disclosure generally relates to vehicle lighting systems, and more particularly, to vehicle lighting systems employing photoluminescent structures.

BACKGROUND OF THE INVENTION

Illumination arising from photoluminescent materials offers a unique and attractive viewing experience. The application provides for various embodiments to incorporate a photoluminescent material in a vehicle component as provided in the following detailed description.

SUMMARY OF THE INVENTION

According to one aspect of the present disclosure, an illumination apparatus for a vehicle is disclosed. The illumination apparatus comprises a wear component comprising a plurality of layers disposed in an engine compartment. The layers comprise a photoluminescent portion and a cover layer disposed over the photoluminescent portion. The apparatus further comprises a light source located in the engine compartment. The light source is configured to emit an excitation emission configured to illuminate the photoluminescent portion to emit an output emission having a color different than the excitation emission.

According to another aspect of the present disclosure, a method of detecting wear in a vehicle component is disclosed. The method comprises utilizing a photoluminescent material in a wear component beneath a cover layer and submitting the wear component to friction until the cover layer is worn creating an exposed surface comprising the photoluminescent material. The method further comprises illuminating the exposed surface with an excitation emission in a first color. In response to the excitation emission, the method continues by exciting the photoluminescent material illuminating the exposed surface in a second color.

These and other aspects, objects, and features of the present disclosure will be understood and appreciated by those skilled in the art upon studying the following specification, claims, and appended drawings.

DETAILED DESCRIPTION OF THE PREFERRED EMBODIMENTS

As required, detailed embodiments of the present disclosure are disclosed herein.

However, it is to be understood that the disclosed embodiments are merely exemplary of the disclosure that may be embodied in various and alternative forms. The figures are not necessarily to a detailed design and some schematics may be exaggerated or minimized to show function overview. Therefore, specific structural and functional details disclosed herein are not to be interpreted as limiting, but merely as a representative basis for teaching one skilled in the art to variously employ the present disclosure.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

The following disclosure describes a lighting system for a vehicle configured to illuminate at least a portion of an engine compartment. In some implementations, a light source may be configured to illuminate a first photoluminescent portion. The first photoluminescent portion may be incorporated as a portion or layer of a vehicle component that may wear over time. Due to the wear of the vehicle component, one or more wear indicating layers of the vehicle component may become visible over time. The first photoluminescent portion may be incorporated in the wear indicating layers such that a photoluminescent structure of the wear indicating layer is exposed to the light source. In this configuration, the light source may excite the photoluminescent structure of the first photoluminescent portion to provide a visible indication of the wear indicating layer being exposed. In this configuration, the wear of the vehicle components may be visibly apparent and easily identified as an indication of a maintenance or service necessary for the vehicle component.

Figure 1:
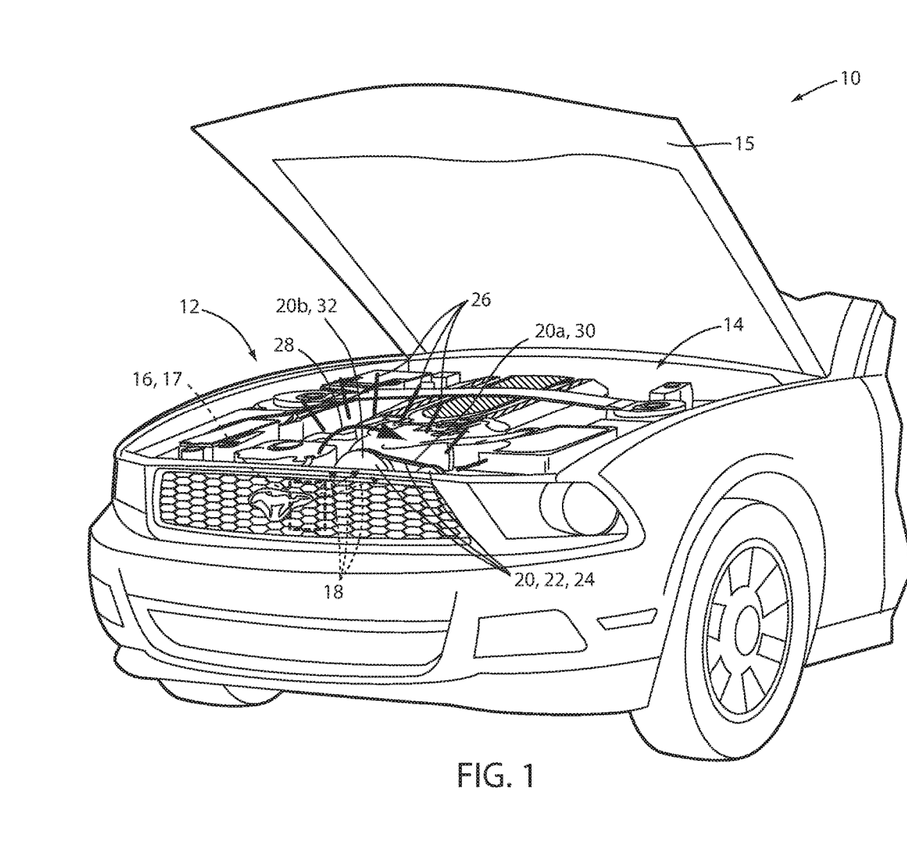
FIG. 1 is a perspective view of a vehicle engine compartment comprising a lighting system.

Referring to FIG. 1, a perspective view of a vehicle 10 is shown demonstrating a lighting system 12 configured to illuminate a portion of an engine compartment 14. The lighting system 12 may be configured to selectively illuminate in response to an open or ajar status of a deck-lid 15 of the vehicle 10 and an ignition of the vehicle 10. In response to the open status of the deck-lid 15 and/or the ignition of the vehicle 10, a controller of the lighting system 12 may activate a light source 16. When activated, the light source 16 may emit an excitation emission 18 configured to illuminate a photoluminescent portion 20, which may be incorporated in a wear component 22 of the vehicle 10. In order to illuminate the wear component 22, the light source 16 may be disposed on an interior surface 17 within the engine compartment 14.

The lighting system 12 may comprise the photoluminescent portion 20 disposed on a wear component 22 of the vehicle 10. The wear component 22 may correspond to a component in the engine compartment 14 that may deteriorate and shed portions or layers of material over time due to deterioration and/or wear (e.g., a belt or pulley). In some embodiments, the light source 16 may be configured to illuminate a layer or wear indicating portion 24 of the wear component 22 with the excitation emission 18. The wear indicating portion 24 may become exposed due to deterioration or wear. In this configuration, the excitation emission 18 may illuminate the photoluminescent portion 20 of the wear component 22 such that a level of wear may be apparent based on the exposure of the wear indicating portion 24 to the excitation emission 18. In response to receiving the excitation emission 18, the photoluminescent portion 20 may emit an output emission 26 in a color of light different from the excitation emission 18. In this way, the lighting system 12 may illuminate the photoluminescent portion 20 such that a luminescent wear layer or the wear indicating portion 24 illuminates to indicate a wear level of the wear component 22.

The wear component 22 may correspond to a component, part, or assembly located proximate the engine compartment 14 or various vehicle compartments. The wear component 22 may move within the engine compartment 14 in a cyclic or rotating motion 28. The motion 28 may result in friction and/or deterioration of the wear components 22 due to the operation of the vehicle 10. The wear component 22 may correspond to a belt 30, pulley 32, or various other moving components of the vehicle that may experience wear due to operation. As discussed herein, the system 12 may provide for accurate visual inspection of the wear component 22 by illuminating the wear indicating portions 24 that have been exposed due to wear.

For example, at the beginning of the lifetime of the wear component 22, the wear indicating portion 24 may be covered or embedded within a multi-layered structure. However, over time the wear level of the wear component 22 may exceed a use threshold resulting in one or more layers of the multi-layered structure being worn away, exposing the wear indicating portion 24. Accordingly, once the wear indicating portion 24 is exposed, the photoluminescent material of the photoluminescent portion 20 may emit the output emission 26 in a color of light different from the excitation emission 18 to provide a visible indication that the use threshold of the wear component 22 has been exceeded. Further details describing an exemplary embodiment of the multi-layer structure of the wear component 22 are provided in reference to FIG. 5.

In some embodiments, the vehicle 10 may comprise a plurality of the wear components 22. In such embodiments, each of the wear components 22 may comprise one or more photoluminescent portions 20. Each of the photoluminescent portions 20 may be applied to or form a portion of any number of the wear components 22 and may incorporate various forms of photoluminescent structures. In an exemplary embodiment, the lighting system 12 may comprise a first photoluminescent portion 20*a* and a second photoluminescent portion 20*b*. Each of the photoluminescent portions 20 may emit output emissions 26 in one or more colors in response to receiving the excitation emission 18 from the light source 16.

The photoluminescent portions 20 may incorporate one or more photoluminescent structures configured to emit a specific color in response to receiving the excitation emission 18. In some implementations, a combination of photoluminescent structures may be utilized in the photoluminescent portions 20 to output various wavelengths corresponding to different colors of light. Accordingly, the lighting system 12 may provide various benefits including a cost-effective method for illuminating the wear indicating portions 24 of the wear components 22 to identify if replacement or maintenance of the wear components 22 may be desirable.

Figure 2A:
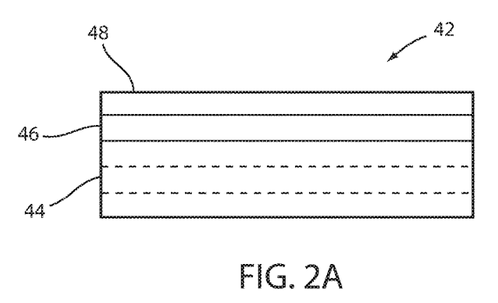
FIG. 2A illustrates a photoluminescent structure rendered as a coating.
Figure 2B:
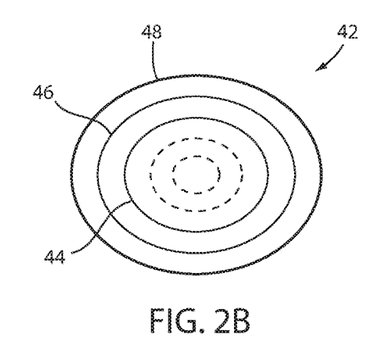
FIG. 2B illustrates the photoluminescent structure rendered as a discrete particle.
Figure 2C:
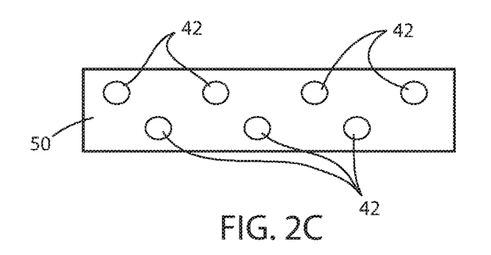
FIG. 2C illustrates a plurality of photoluminescent structures rendered as discrete particles and incorporated into a separate structure.

Referring to FIGS. 2A-2C, a photoluminescent structure 42 is generally shown rendered as a coating (e.g., a film) capable of being applied to a vehicle component (e.g., the wear component 22), a discrete particle capable of being implanted in a vehicle component, and a plurality of discrete particles incorporated into a separate structure capable of being applied to a vehicle component, respectively. The photoluminescent structure 42 may correspond to the photoluminescent portions 20 as discussed herein, for example, the first photoluminescent portion 20*a* and the second photoluminescent portion 20*b*. At the most basic level, the photoluminescent structure 42 may include an energy conversion layer 44 that may be provided as a single layer or a multi-layer structure, as shown through broken lines in FIGS. 2A and 2B.

The energy conversion layer 44 may include one or more photoluminescent materials having energy converting elements selected from a phosphorescent or a fluorescent material. The photoluminescent materials may be formulated to convert an inputted electromagnetic radiation into an outputted electromagnetic radiation generally having a longer wavelength and expressing a color that is not characteristic of the inputted electromagnetic radiation. The difference in wavelength between the inputted and outputted electromagnetic radiations is referred to as the Stokes shift and serves as the principle driving mechanism for an energy conversion process corresponding to a change in wavelength of light, often referred to as down conversion. In the various implementations discussed herein, each of the wavelengths of light (e.g., the first wavelength, etc.) correspond to electromagnetic radiation utilized in the conversion process.

Each of the photoluminescent portions 20 may comprise at least one photoluminescent structure 42 comprising an energy conversion layer (e.g., conversion layer 44). The energy conversion layer 44 may be prepared by dispersing the photoluminescent material in a polymer matrix 50 to form a homogenous mixture using a variety of methods. Such methods may include preparing the energy conversion layer 44 from a formulation in a liquid carrier medium and utilizing the energy conversion layer 44 as an integral portion of the multi-layered structure of the wear component 22. Additionally, the energy conversion layer 44 may be prepared by methods that do not use a liquid carrier medium.

For example, a solid-state solution (homogenous mixture in a dry state) of one or more photoluminescent materials may be incorporated in a polymer matrix 50 to provide the energy conversion layer 44. The polymer matrix 50 may be formed by extrusion, injection molding, compression molding, calendaring, thermoforming, etc. In instances where one or more energy conversion layers 44 are rendered as particles, the single or multi-layered energy conversion layers 44 may be implanted into the wear component 22. When the energy conversion layer 44 includes a multi-layer formulation, each layer may be sequentially coated. Additionally, the layers can be separately prepared and later laminated or embossed together to form an integral layer. The layers may also be coextruded to prepare an integrated multi-layered energy conversion structure.

Referring back to FIGS. 2A and 2B, the photoluminescent structure 42 may optionally include at least one stability layer 46 to protect the photoluminescent material contained within the energy conversion layer 44 from photolytic and thermal degradation. The stability layer 46 may be configured as a separate layer optically coupled and adhered to the energy conversion layer 44. The stability layer 46 may also be integrated with the energy conversion layer 44. The photoluminescent structure 42 may also optionally include a protective layer 48 optically coupled and adhered to the stability layer 46 or any layer or coating to protect the photoluminescent structure 42 from physical and chemical damage arising from environmental exposure.

In some implementations, the photoluminescent structure 42 may be incorporated into the wear component 22 as one or more discrete multi-layered particles as shown in FIG. 2C. The photoluminescent structure 42 may also be provided as one or more discrete multi-layered particles dispersed in a polymer formulation that is subsequently applied to the wear component 22 as a contiguous structure. Additional information regarding the construction of photoluminescent structures to be utilized in at least one photoluminescent portion of a vehicle is disclosed in U.S. Pat. No. 8,232,533 to Kingsley et al., entitled "PHOTOLYTICALLY AND ENVIRONMENTALLY STABLE MULTILAYER STRUCTURE FOR HIGH EFFICIENCY ELECTROMAGNETIC ENERGY CONVERSION AND SUSTAINED SECONDARY EMISSION," filed Nov. 8, 2011, the entire disclosure of which is incorporated herein by reference.

Figure 3:
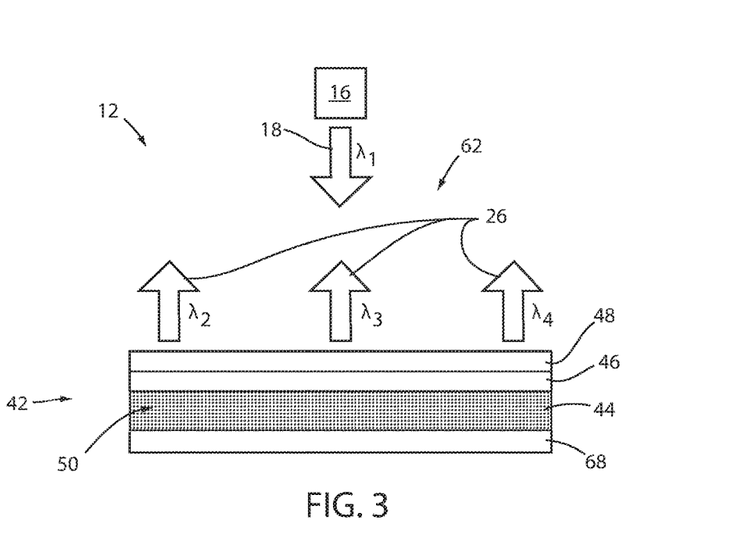
FIG. 3 illustrates a vehicle lighting system configured to convert a first emission of light to a second emission of light.

Referring to FIG. 3, the lighting system 12 is generally shown according to a front-lit configuration 62 to convert the excitation emission 18 from the light source 16 to the output emission 26. The excitation emission 18 may comprise a first wavelength $\lambda_1$, and the output emission 26 may comprise at least a second wavelength $\lambda_2$. The lighting system 12 may include the photoluminescent structure 42 rendered as a coating and applied to a one or more layers 68 of the multi-layered structure of the wear component 22. The photoluminescent structure 42 may include the energy conversion layer 44, and in some implementations may include the stability layer 46 and/or protective layer 48. In response to the light source 16 being activated, the excitation emission 18 is converted from the first wavelength $\lambda_1$ to the output emission 26 having at least the second wavelength $\lambda_2$. The output emission 26 may comprise a plurality of wavelengths $\lambda_2$, $\lambda_3$, $\lambda_4$ configured to emit significantly white light from the wear component 22.

In various implementations, the lighting system 12 comprises at least one energy conversion layer 44 configured to convert the excitation emission 18 at the first wavelength $\lambda_1$ to the output emission 26 having at least the second wavelength $\lambda_2$. In order to generate the plurality of wavelengths $\lambda_2$, $\lambda_3$, $\lambda_4$, the energy conversion layer 44 may comprise a red-emitting photoluminescent material, a green-emitting photoluminescent material, and a blue-emitting photoluminescent material. The red, green, and blue-emitting photoluminescent materials may be combined to generate the significantly white light for the output emission 26. Further, the red, green, and blue-emitting photoluminescent materials may be utilized in a variety of proportions and combinations to control the color of the output emission 26.

Each of the photoluminescent materials may vary in output intensity, output wavelength, and peak absorption wavelengths based on a particular photochemical structure and combinations of photochemical structures utilized in the energy conversion layer 44. As an example, the output emission 26 may be changed by adjusting the wavelength of the first emission $\lambda_1$ to activate the photoluminescent materials at different intensities to alter the color of the output emission 26. In addition to, or alternatively to, the red, green, and blue-emitting photoluminescent materials, other photoluminescent materials may be utilized alone and in various combinations to generate the output emission 26 in a wide variety of colors. In this way, the lighting system 12 may be configured for a variety of applications to provide a desired lighting color and effect for the vehicle 10.

The light source 16 may also be referred to as an excitation source and is operable to emit at least the excitation emission 18. The light source 16 may comprise any form of light source, for example, halogen lighting, fluorescent lighting, light-emitting diodes (LEDs), organic LEDs (OLEDs), polymer LEDs (PLEDs), solid-state lighting, or any other form of lighting configured to output the excitation emission 18. The excitation emission 18 from the light source 16 may be configured such that the first wavelength $\lambda_1$ corresponds to at least one absorption wavelength of the one or more photoluminescent materials of the energy conversion layer 44. In response to receiving the light at the first wavelength $\lambda_1$, the energy conversion layer 44 may be excited and output the one or more output wavelengths $\lambda_2$, $\lambda_3$, $\lambda_4$. The excitation emission 18 provides an excitation source for the energy conversion layer 44 by targeting absorption wavelengths of the various photoluminescent materials utilized therein. As such, the lighting system 12 is configured to output the output emission 26 to generate a desired light intensity and color.

Though the plurality of wavelengths is referred to as the wavelengths $\lambda_2$, $\lambda_3$, $\lambda_4$, the photoluminescent materials may be combined in various proportions, types, layers, etc. to generate a variety of colors for the output emission 26. The photoluminescent materials may also be utilized in a plurality of photoluminescent portions 20 distributed along a path of the excitation emission 18 to generate any number of emissions.

In an exemplary implementation, the light source 16 comprises an LED configured to emit the first wavelength $\lambda_1$ which corresponds to a blue spectral color range. The blue spectral color range comprises a range of wavelengths generally expressed as blue light (~440-500 nm). In some implementations, the first wavelength $\lambda_1$ may also comprise wavelengths in a near ultraviolet color range (~390-450 nm). In an exemplary implementation, $\lambda_1$ may be approximately equal to 470 nm. In some implementations, the first wavelength $\lambda_1$ may be approximately less than 500 nm such that the first wavelength of the light is not significantly visible.

The blue spectral color range and shorter wavelengths may be utilized as an excitation source for the lighting system 12 due to these wavelengths having limited perceptual acuity in the visible spectrum of the human eye. By utilizing shorter wavelengths for the first wavelength $\lambda_1$, and converting the first wavelength with the conversion layer 44 to at least one longer wavelength, the lighting system 12 creates a visual effect of light originating from the photoluminescent structure 42. In this configuration, light is emitted from the photoluminescent structure 42 (e.g., the first photoluminescent portion 20a, the second photoluminescent portion 20b) from locations of the vehicle 10 that may be inaccessible or costly to add conventional light sources requiring electrical connections.

As discussed herein, each of the plurality of wavelengths $\lambda_2$, $\lambda_3$, $\lambda_4$ may correspond to a significantly different spectral color range. The second wavelength $\lambda_2$ may correspond to the excitation of a red-emitting photoluminescent material having a wavelength of approximately 620-750 nm. The third wavelength $\lambda_3$ may correspond to the excitation of a green emitting photoluminescent material having a wavelength of approximately 526-606 nm. The fourth wavelength $\lambda_4$ may correspond to a blue or blue green emitting photo luminescent material having a wavelength longer than the first wavelength $\lambda_1$ and approximately 430-525 nm. Though the wavelengths $\lambda_2$, $\lambda_3$, $\lambda_4$ are discussed herein as being utilized to generate a significantly white light, various combinations of photoluminescent materials may be utilized in the conversion layer 44 to convert the first wavelength $\lambda_1$ to one or more wavelengths corresponding to a variety of colors.

Figure 4:
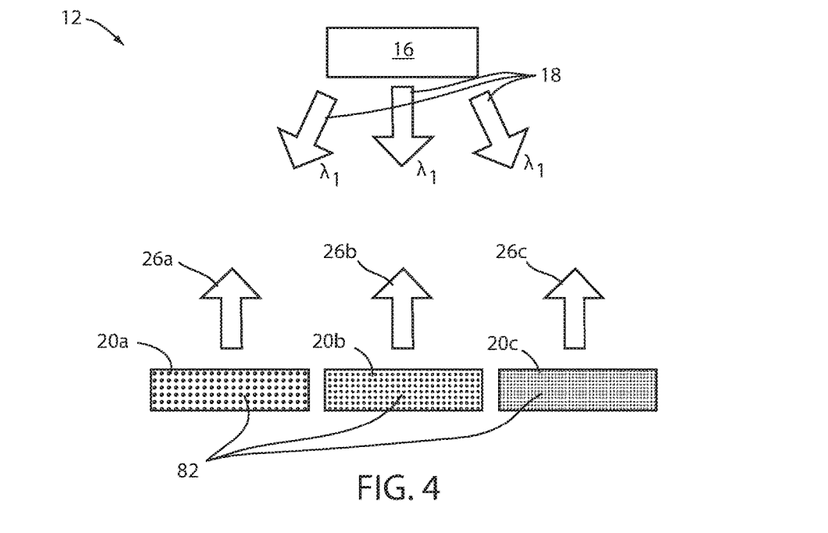
FIG. 4 illustrates the vehicle lighting system configured to convert a first emission of light to a plurality of emissions of light.

Referring to FIG. 4, the lighting system 12 is shown in a front-lit configuration 62. In an exemplary implementation, the light source 16 may be configured to emit the excitation emission 18 toward the plurality of photoluminescent portions 20. In this example, the plurality of photoluminescent portions 20 comprises the first photoluminescent portion 20a, the second photoluminescent portion 20b and may further comprise a third photoluminescent portion 20c. Each of the photoluminescent portions 20 may be configured to convert the first wavelength $\lambda_1$ of the excitation emission 18 to one or more of the plurality of wavelengths $\lambda_2$, $\lambda_3$, $\lambda_4$. In this way, the excitation emission 18 may be converted into a plurality of output emissions 26 originating from each of the photoluminescent portions 20 to generate a multi-colored lighting effect.

For example, the first photoluminescent portion 20a may comprise photoluminescent materials in a conversion layer configured to generate a first output emission 26a. The second photoluminescent portion 20b may comprise photoluminescent materials in a conversion layer configured to generate a second output emission 26b. The third photoluminescent portion 20c may comprise photoluminescent materials in a conversion layer configured to generate a third output emission 26c. Similar to the energy conversion layer 44, discussed in reference to FIG. 3, photoluminescent materials configured to emit light of various colors may be utilized in a variety of proportions and combinations to control the output color of each of the output emissions 26. Based on a desired lighting effect, each of the output emissions 26 may comprise photoluminescent material configured to emit light having substantially similar colors or a wide variety of color combinations.

To achieve the various colors and combinations of photoluminescent materials described herein, the lighting system 12 may utilize any form of photoluminescent materials, for example, phospholuminescent materials, organic and inorganic dyes, etc. For additional information regarding fabrication and utilization of photoluminescent materials to achieve various emissions, refer to U.S. Pat. No. 8,207,511 to Bortz et al., entitled "PHOTOLUMINESCENT FIBERS, COMPOSITIONS AND FABRICS MADE THEREFROM," filed Jun. 5, 2009; U.S. Pat. No. 8,247,761 to Agrawal et al., entitled "PHOTOLUMINESCENT MARKINGS WITH FUNCTIONAL OVERLAYERS," filed Oct. 19, 2011; U.S. Pat. No. 8,519,359 B2 to Kingsley et al., entitled "PHOTOLYTICALLY AND ENVIRONMENTALLY STABLE MULTILAYER STRUCTURE FOR HIGH EFFICIENCY ELECTROMAGNETIC ENERGY CONVERSION AND SUSTAINED SECONDARY EMISSION," filed Mar. 4, 2013; U.S. Pat. No. 8,664,624 B2 to Kingsley et al., entitled "ILLUMINATION DELIVERY SYSTEM FOR GENERATING SUSTAINED SECONDARY EMISSION," filed Nov. 14, 2012; U.S. Patent Application Publication No. 2012/0183677 to Agrawal et al., entitled "PHOTOLUMINESCENT COMPOSITIONS, METHODS OF MANUFACTURE AND NOVEL USES," filed Mar. 29, 2012; U.S. Pat. No. 9,057,021 to Kingsley et al., entitled "PHOTOLUMINESCENT OBJECTS," filed Oct. 23, 2012; and U.S. Pat. No. 9,493,699 to Agrawal et al., entitled "CHROMIC LUMINESCENT COMPOSITIONS AND TEXTILES," filed Dec. 19, 2012, all of which are included herein by reference in their entirety.

Figure 5:
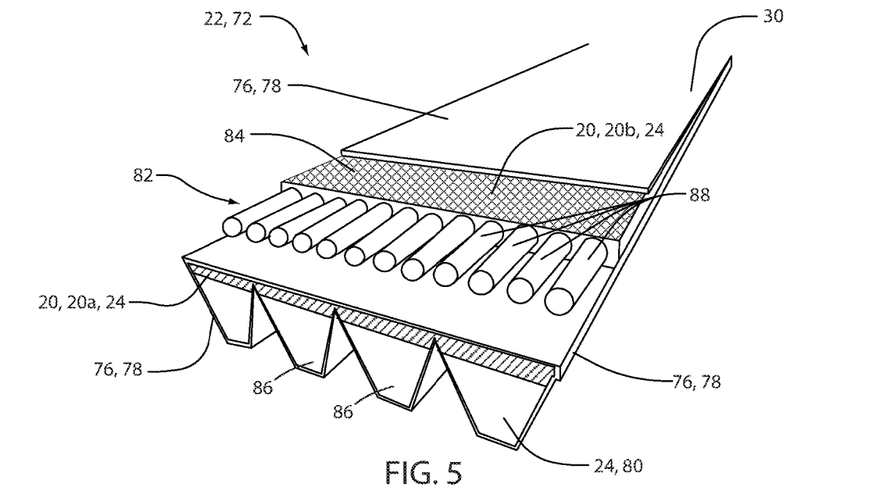
FIG. 5 is a perspective view of a drive belt of a vehicle configured to illuminate to indicate wear.

Referring to FIG. 5, a perspective view of a multi-layered structure 72 of the wear component 22 of the vehicle 10 is shown. In an exemplary embodiment, the wear component 22 may correspond to a belt 30, which may be configured to distribute power to a variety of parts of an engine or related operational components of the vehicle 10. The multi-layered structure 72 may comprise one or more exterior layers 76, which may cover or enclose the wear indicating layer or wear indicating portion 24. Once the exterior layers 76 of the belt 30 deteriorate due to friction and material deterioration, the wear indicating portion 24 may become exposed such that the excitation emission 18 impinges upon the photoluminescent material of the photoluminescent portion 20. In response to the excitation emission 18, the photoluminescent portion 20 may emit the output emission 26 in a color of light different from the excitation emission 18 to provide a visible indication that a wear threshold of the wear component 22 has been exceeded.

The multi-layered structure 72 of the wear component 22 may comprise a cover layer 78, which may correspond to the one of the exterior layers 76. The cover layer 78 may correspond to a rubber impregnated fabric configured to provide friction resistance and may enclose the belt forming at least a portion of the exterior layers 76. Beneath the cover layer 78, the multi-layered structure 72 may further comprise a compression layer 80, a tensile cord layer 82, and an insulation layer 84 or adhesion layer. The compression layer 80 may form and comprise a plurality of grooves 86 formed of rubber or fiber loaded rubber material. The tensile cord layer 82 may comprise a plurality of cords 88, which may be of polyester, carbon, or a variety of materials resilient to fatigue. The plurality of cords 88 may extend along a length of the wear component 22 to provide tensile strength. The insulation layer 84 may be of a polymeric material configured to adhere or laminate the plurality of cords 88 to the compression layer 80.

In various embodiments, the photoluminescent portion 20 or portions may be disposed beneath the cover layer 78 and/or as integral layers incorporated in one or more of the layers of the multi-layered structure 72. For example, in some embodiments, the first photoluminescent portion 20a may form a portion of the compression layer 80. In this configuration, the first output emission 26a may be emitted from the first photoluminescent portion 20a in response to receiving the excitation emission 18. Accordingly, the first output emission 26a may provide a visible indication that the cover layer 78 and/or the compression layer 80 are worn to the extent that the first photoluminescent portion 20a is exposed to the excitation emission 18.

In some embodiments, the second photoluminescent portion 20b may form a portion of the tensile cord layer 82 and/or the insulation layer 84. In this configuration, the second output emission 26b may be emitted from the second photoluminescent portion 20b in response to receiving the excitation emission 18. Accordingly, the emission of the second output emission 26b may provide a visible indication that the cover layer 78 and/or the insulation layer 84 are worn to the extent that the second photoluminescent portion 20b is exposed to the excitation emission 18. Accordingly, the multi-layered structure 72 of the wear component 22 may comprise one or more of the photoluminescent portions 20 such that the output emissions 26 may emit a visible indication of the wear level of the component 22 in response to one or more of the photoluminescent portions 20 being exposed to the excitation emission 18.

Figure 6:
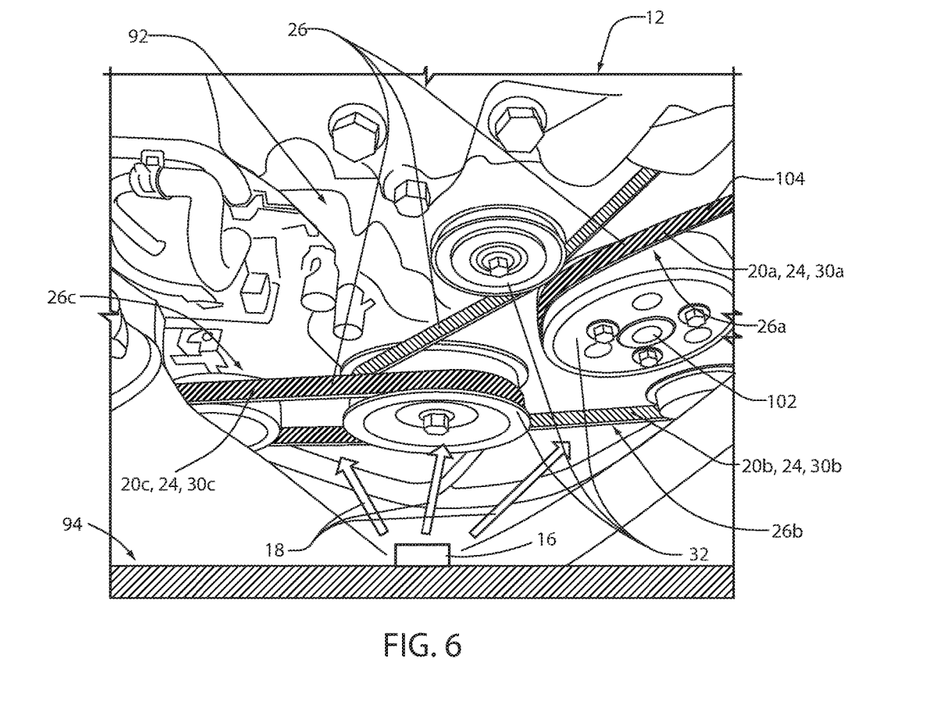
FIG. 6 is a perspective view of a vehicle engine compartment comprising a lighting apparatus configured to illuminate a wear component.

Referring now to FIG. 6, a perspective view of the engine block 92 is shown disposed in the engine compartment 14 of the vehicle 10. In operation, the light source 16 may be activated by a controller of the lighting system 12 to illuminate one or more of the wear components 22. In the exemplary embodiment demonstrated in FIG. 6, the light source 16 is disposed on the surface 17 located inside the engine compartment 14 proximate a radiator 94. Accordingly, the light source 16 may be disposed proximate an opening or space formed between the radiator 94 and engine block 92. In some embodiments, the light source 16 may be disposed proximate a grill, a hood latch, or various surfaces from which the excitation emission 18 may illuminate the belt 30, pulley 32, or various wear components 22.

In some embodiments, one or more of the wear components 22 may comprise the plurality of photoluminescent portions 20. The plurality of photoluminescent portions 20 may be incorporated in a plurality of belts 30, pulleys 32, or various additional wear components 22 of the vehicle 10. For example, the belts 30 may comprise a first photoluminescent portion 20a disposed in a first belt 30a, the second photoluminescent portion 20b disposed in a second belt 30b, and a third photoluminescent portion 20c disposed in a third belt 30c. As previously discussed, each of the photoluminescent portions 20a, 20b, and 20c may emit the first output emission 26a, the second output emission 26b, and the third output emission 26c as different colors based on the photoluminescent materials utilized to form the photoluminescent portions 20a, 20b, and 20c. Accordingly, the color of the photoluminescent portions 20a, 20b, and 20c may also provide for a color coded identification of the belts 30 to further assist in maintenance and identification.

Figure 7:
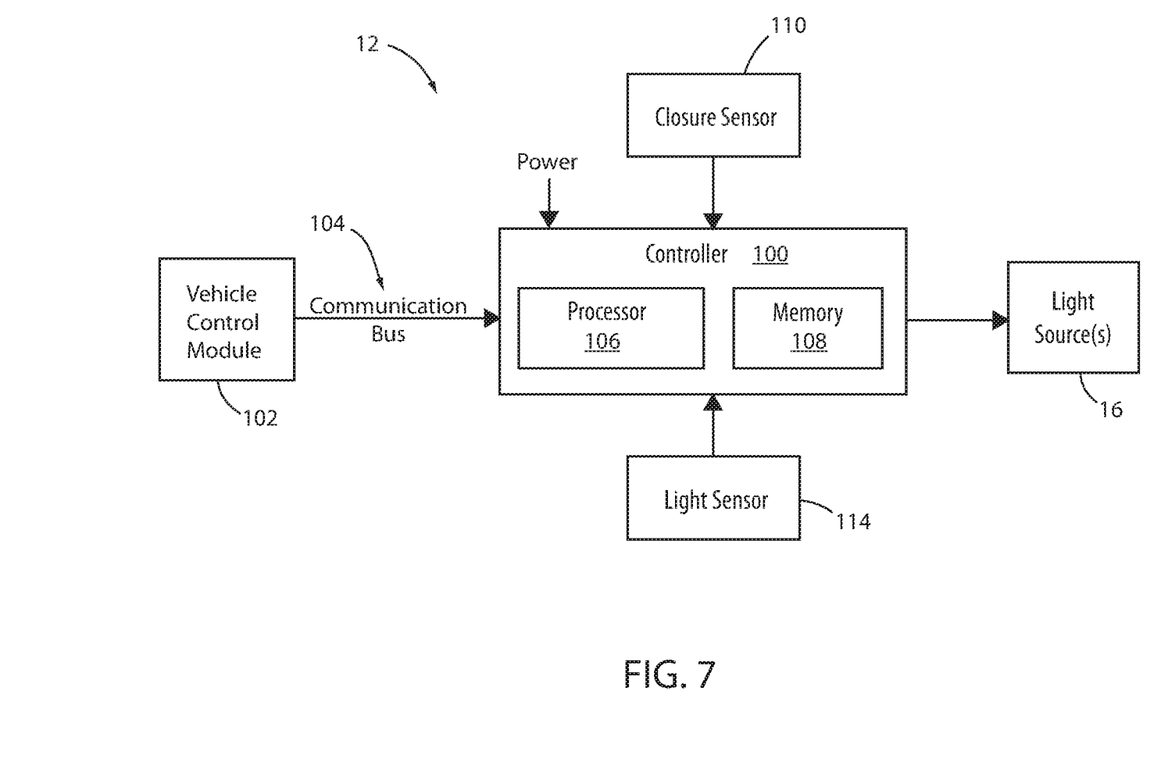
FIG. 7 is a block diagram of a vehicle lighting system configured to illuminate a wear component in an engine compartment.

Referring now to FIG. 7, a block diagram of the lighting system 12 is shown. The lighting system 12 may comprise the controller 100 configured to control the light source 16. The controller 100 may be in communication with a vehicle control module 102 via a communication bus 104 of the vehicle 10. The communication bus 104 may be configured to deliver signals to the controller 100 identifying various states of the vehicle 10. For example, the communication bus 104 may be configured to communicate an operating condition of the vehicle 10 (e.g., the ignition is active), an ambient light level, a door ajar signal, a gear selection, a door lock/unlock event, an open or closed status of engine compartment 14 or any other information or control signals that may be communicated via the communication bus 104. In this way, the controller 100 may selectively activate the active light source 16 in response to one or more conditions communicated by the vehicle control module 102.

The controller 100 may include a processor 106 comprising one or more circuits configured to receive the signals from the communication bus 104 and output signals to control the light source 16 as discussed herein. The processor 106 may be in communication with a memory 108 configured to store instructions to control the activation of the light source 16. The processor 106 may receive various signals and/or messages corresponding to vehicle conditions via the communication bus 104. In this way, the controller 100 may be configured to receive an indication of an ajar status of the deck-lid 15 of the vehicle 10 communicated via a status signal communicated via from a closure sensor 110.

The closure sensor 110 may correspond to a proximity sensor and/or presence sensor utilizing various forms of technology to detect the ajar status of the deck-lid 15. For example, the closure sensor 110 may correspond to a capacitive sensor, inductive sensor, laser or optical based sensor, or any suitable form of sensor that may detect the open state of the deck-lid 15. The closure sensor 110 may be in direct communication with or integrated with the controller 100, and may also be in communication with the controller 100 via the control module 102 via the communication bus 104. As discussed herein, the lighting system 12 may be implemented in a variety of ways to provide for various configurations without departing from the spirit of the disclosure.

In some embodiments, the controller 100 may be utilized to illuminate that light source 16 for a diagnostic process. For example, in response to a user input received via the communication bus 104, the controller 100 may activate a diagnostic mode. In the diagnostic mode, the controller 100 may control the light source 16 to activate for an inspection of the wear components 22. Accordingly as the light source 16 may be activated in response to the user input to provide a visual indication in the form of the output emission(s) 26 to assist in the identification of the wear of the cover layer 78 or any of the layers of the multi-layered structure 72 as discussed herein.

The controller 100 may further be in communication with a light sensor 114. The light sensor 114 may be configured to communicate a signal to the controller 100 such that the controller 100 may identify a light level of the output emissions 26 proximate the wear components 22. Accordingly, the light sensor 114 may be configured to identify the presence of the wavelengths of light emitted from the photoluminescent portions 20. For example, the light sensor 114 may be configured to detect the wavelengths of light emitted from the photoluminescent portions 20 in response to the excitation emission 18 activating the output emissions 26. The light sensor 114 may correspond to various forms of sensors, for example, charge-coupled devices CCDs, photodiodes, etc. Based on the input from the sensor 114, the controller 100 may be operable to identify the presence of the wavelengths associated with the photoluminescent portions 20 and output an indication that the vehicle 10 may require maintenance due to the wear of one of more of the wear components 22.

According to one aspect of the present disclosure, an illumination apparatus for a vehicle is disclosed. The illumination apparatus comprises a wear component comprising a plurality of layers disposed in an engine compartment. The layers comprise a photoluminescent portion and a cover layer disposed over the photoluminescent portion. The apparatus further comprises a light source located in the engine compartment. The light source is configured to emit an excitation emission configured to illuminate the photoluminescent portion to emit an output emission having a color different than the excitation emission.

Embodiments of the one aspect of the invention can include any one or a combination of the following features: the cover layer encloses the photoluminescent portion such that the excitation emission does not impinge upon the photoluminescent portion; the cover layer is configured to wear away from the wear component forming an exposed surface of the photoluminescent portion; the light source is configured to direct the excitation emission toward the exposed surface of the wear component generating the output emission; the output emission is emitted from the exposed surface in the engine compartment providing an illuminated indication of a wear condition of the wear component; the plurality of layers comprises a compression layer; the compression layer forms a plurality of grooves configured to engage a pulley of an engine; the photoluminescent portion forms at least a portion of the compression layer; the plurality of layers comprises a cord layer enclosed in an insulation layer; the cord layer comprises a plurality of cords extending along a length of the wear component; the insulation layer is configured to laminate the cord layer to the compression layer; the photoluminescent portion forms at least a portion of the insulation layer; the photoluminescent portion forms at least a portion of the cord layer; the photoluminescent portion comprises a plurality of photoluminescent portions; and/or the plurality of photoluminescent portions are disposed on more than one of the plurality of the layers of the wear component beneath the cover layer.

According to another aspect of the present disclosure, a method of detecting wear in a vehicle component is disclosed. The method comprises utilizing a photoluminescent material in a wear component beneath a cover layer and submitting the wear component to friction until the cover layer is worn creating an exposed surface comprising the photoluminescent material. The method further comprises illuminating the exposed surface with an excitation emission in a first color. In response to the excitation emission, the method continues by exciting the photoluminescent material illuminating the exposed surface in a second color.

Embodiments of the this aspect of the method can include any one or a combination of the following features: the wear component comprises a belt; the belt is formed of a plurality of layers comprising at least one photoluminescent portion comprising the photoluminescent material and comprising the cover layer forming an exterior layer of the belt; the friction results from the belt passing over a pulley; and/or the method further comprises activating the excitation emission in response to a user input activating a diagnostic process.

For the purposes of describing and defining the present teachings, it is noted that the terms "substantially" and "approximately" are utilized herein to represent the inherent degree of uncertainty that may be attributed to any quantitative comparison, value, measurement, or other representation. The term "substantially" and "approximately" are also utilized herein to represent the degree by which a quantitative representation may vary from a stated reference without resulting in a change in the basic function of the subject matter at issue.

It is to be understood that variations and modifications can be made on the aforementioned structure without departing from the concepts of the present disclosure, and further it is to be understood that such concepts are intended to be covered by the following claims unless these claims by their language expressly state otherwise.

What is claimed is:

1. An illumination apparatus for a vehicle, comprising:
a wear component comprising a plurality of layers configured to be disposed in an engine compartment, the layers comprising a photoluminescent portion and a cover layer configured to erode from an exterior surface of the wear component as a result of usage, wherein the cover layer is configured to suppress an illumination response to an excitation emission comprising a first wavelength of light, the cover layer disposed over the photoluminescent portion, wherein the cover layer encloses the photoluminescent portion and is configured to occlude the photoluminescent portion from the excitation emission; and
a light source configured to be located in the engine compartment, the light source configured to emit the excitation emission configured to illuminate an exposed surface of the photoluminescent portion resulting from the erosion of the cover layer, wherein the exposed surface of the photoluminescent portion is configured to generate an output emission having a second wavelength different from the first wavelength.

2. The apparatus according to claim 1, wherein the output emission is configured to be emitted from the exposed surface in the engine compartment providing an illuminated indication of a wear condition of the wear component.

3. The apparatus according to claim 1, wherein the plurality of layers comprises a compression layer.

4. The apparatus according to claim 3, wherein the compression layer comprises a plurality of grooves configured to engage a pulley of an engine.

5. The apparatus according to claim 3, wherein the photoluminescent portion is incorporated as at least a portion of the compression layer.

6. The apparatus according to claim 3, wherein the plurality of layers comprises a cord layer configured to be enclosed in an insulation layer.

7. The apparatus according to claim 6, wherein the cord layer comprises a plurality of cords extending along a length of the wear component.

8. The apparatus according to claim 6, wherein the insulation layer is configured to laminate the cord layer to the compression layer.

9. The apparatus according to claim 6, wherein the photoluminescent portion forms at least a portion of the insulation layer.

10. The apparatus according to claim 6, wherein the photoluminescent portion forms at least a portion of the cord layer.

11. The apparatus according to claim 1, wherein the photoluminescent portion comprises a plurality of photoluminescent portions.

12. The apparatus according to claim 1, wherein the plurality of photoluminescent portions are configured to be disposed on more than one of the plurality of the layers of the wear component beneath the cover layer.

13. A method of detecting wear in a wear component of a vehicle, comprising:
utilizing a photoluminescent material in the wear component beneath a cover layer, wherein the cover layer is configured to suppress an illumination response to an excitation emission and occlude the photoluminescent portion from the excitation emission;
submitting the wear component to friction until the cover layer is worn creating an exposed surface comprising the photoluminescent material;
illuminating the exposed surface with the excitation emission in a first wavelength; and
exciting the photoluminescent material with the excitation emission illuminating the exposed surface in a second wavelength different from the first wavelength.

14. The method according to claim 13, wherein the wear component comprises a belt.

15. The method according to claim 14, wherein the belt is formed of a plurality of layers comprising at least one photoluminescent portion comprising the photoluminescent material and comprising the cover layer forming an exterior layer of the belt.

16. The method according to claim 14, wherein the friction results from the belt passing over a pulley.

17. The method according to claim 13, further comprising activating the excitation emission in response to a user input activating a diagnostic process.

* * * * *